US008828084B2

(12) United States Patent
Aflatoon et al.

(10) Patent No.: US 8,828,084 B2
(45) Date of Patent: Sep. 9, 2014

(54) DYNAMIC INTERBODY CAGE ANCHOR SYSTEM

(76) Inventors: Kamran Aflatoon, Corona del Mar, CA (US); Chris Maurer, Wakefield, MA (US)

(*) Notice: Subject to any disclaimer, the term of this patent is extended or adjusted under 35 U.S.C. 154(b) by 329 days.

(21) Appl. No.: 13/155,864

(22) Filed: Jun. 8, 2011

(65) Prior Publication Data

US 2012/0143336 A1 Jun. 7, 2012

Related U.S. Application Data

(60) Provisional application No. 61/352,539, filed on Jun. 8, 2010.

(51) Int. Cl.
*A61F 2/44* (2006.01)
(52) U.S. Cl.
USPC ..................... 623/17.16
(58) Field of Classification Search
USPC .............. 606/70, 71, 246–279, 280–299; 623/17.11–17.16
See application file for complete search history.

(56) References Cited

U.S. PATENT DOCUMENTS

| 7,914,561 B2* | 3/2011 | Konieczynski et al. ...... 606/280 |
| 8,287,572 B2* | 10/2012 | Bae et al. ...................... 606/279 |
| 2007/0276386 A1* | 11/2007 | Gerlach et al. .................. 606/72 |
| 2008/0051890 A1* | 2/2008 | Waugh et al. ............... 623/17.11 |
| 2009/0118769 A1* | 5/2009 | Sixto et al. .................... 606/280 |

* cited by examiner

*Primary Examiner* — Christopher Beccia
(74) *Attorney, Agent, or Firm* — Ober, Kaler, Grimes & Shriver; Royal W. Craig; Christopher F. Lonegro

(57) ABSTRACT

A system and method of securing an intervertebral fusion cage within the intervertebral space between adjacent vertebra in which one or more slots are provided in an anterior surface of the cage each extending from an oversized aperture. A retention plate having a post and enlarged head is advanced into each slot via the oversized aperture and captured therein. The post is advanced to the terminal end of the plate and secured to vertebral body at its distal end by a bone screw. A locking clip is slideably positioned on the retention plate to prevent withdrawal of the bone screw. The slots preferably extend to margins of the anterior surface of the cage in, for example, the pattern of an "X" or an "H". Sliding of the posts in the slots prevents the system from carrying the vertebral load (load shielding) and permits reduction in the intervertebral space to promote bone growth and fusion by graft material retained in the spacer.

12 Claims, 4 Drawing Sheets

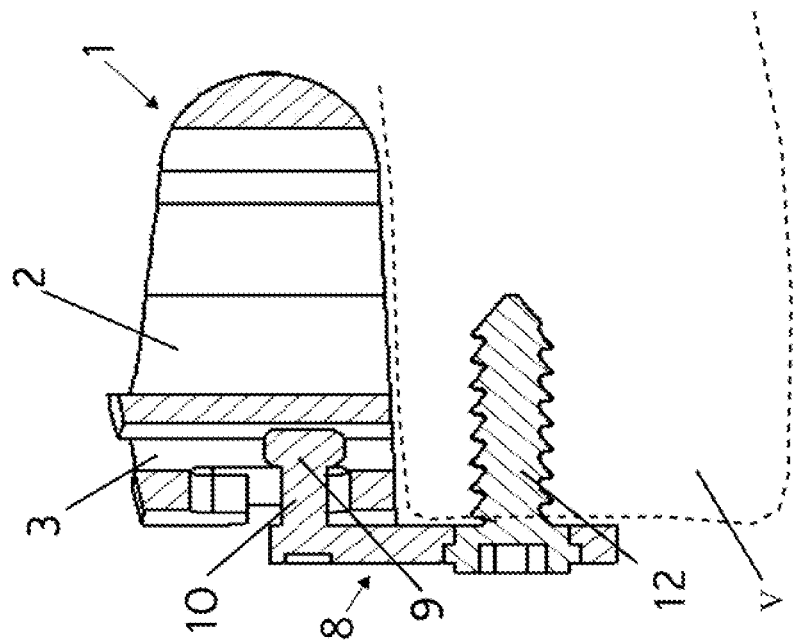
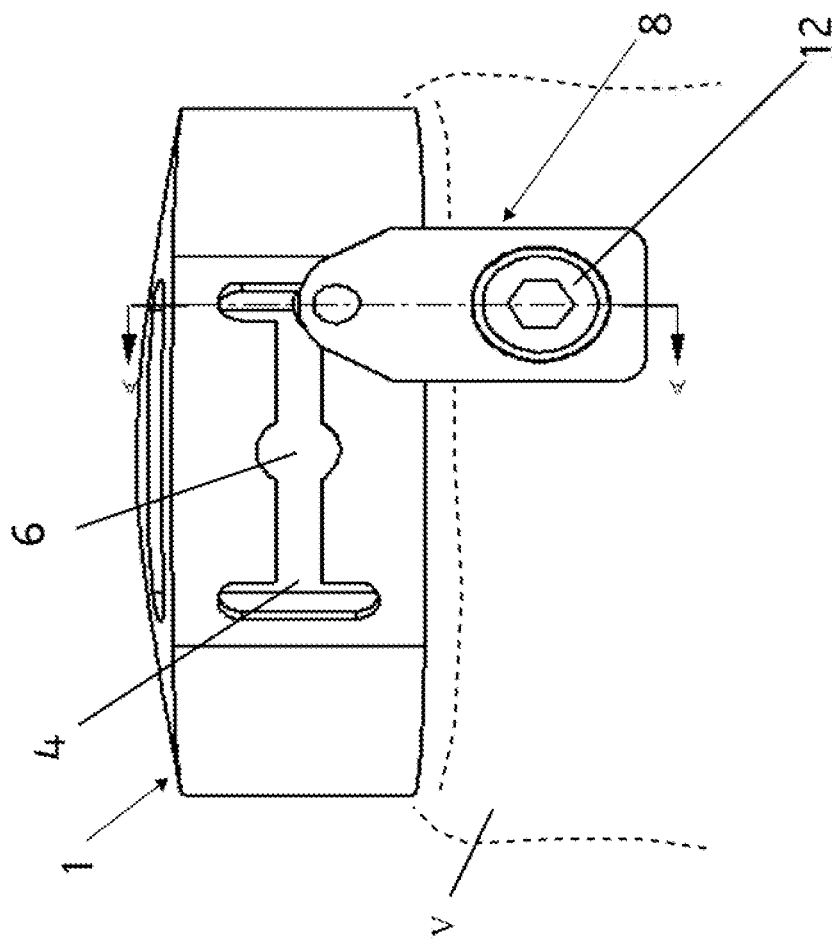
FIG. 2b
FIG. 2a

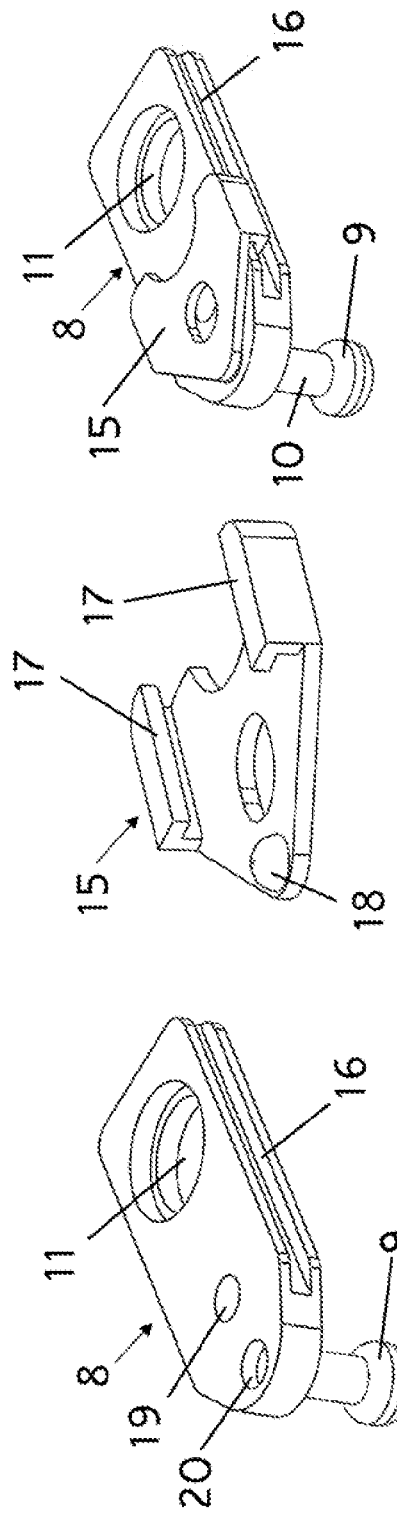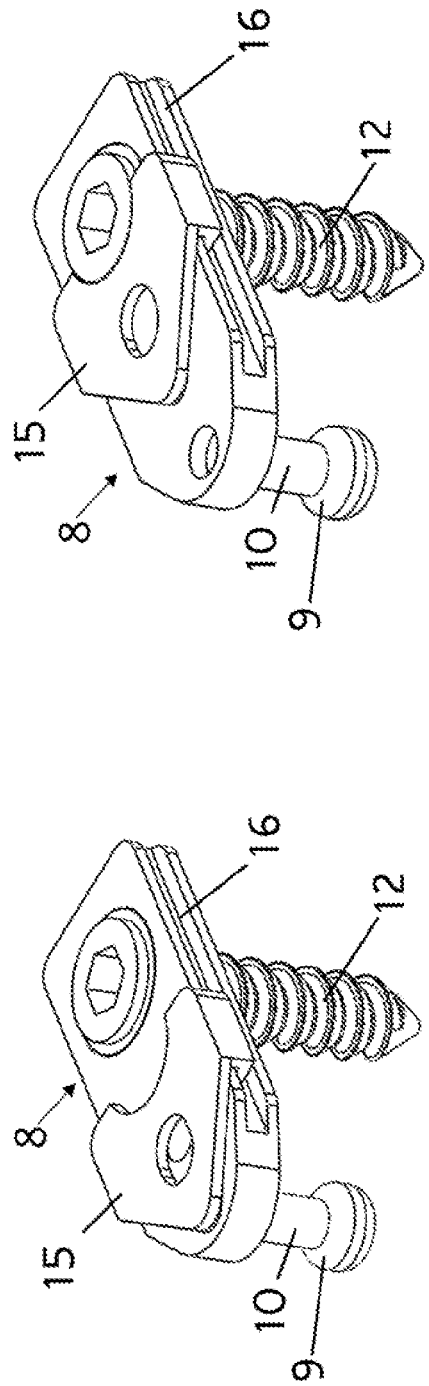

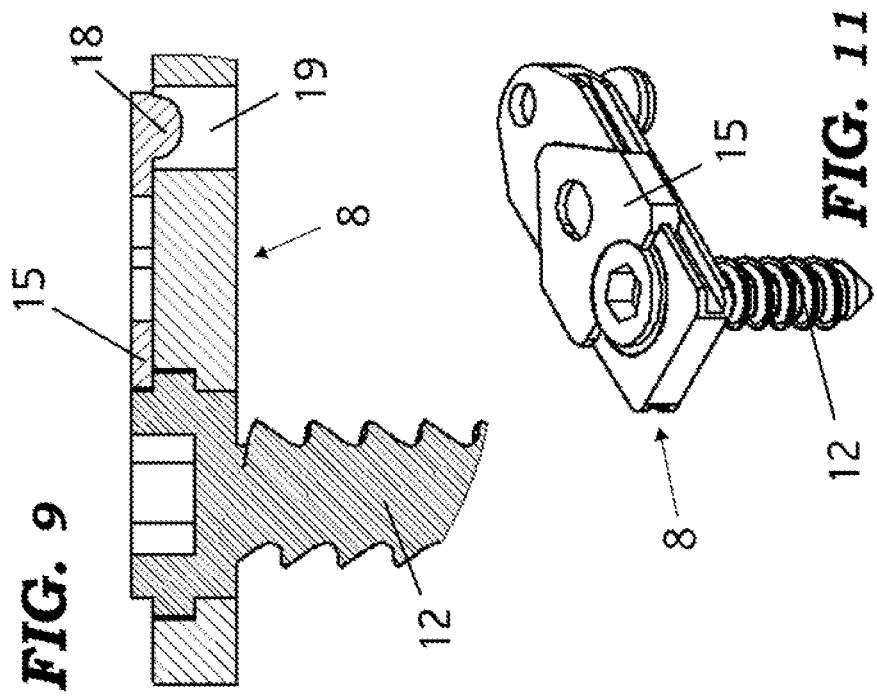
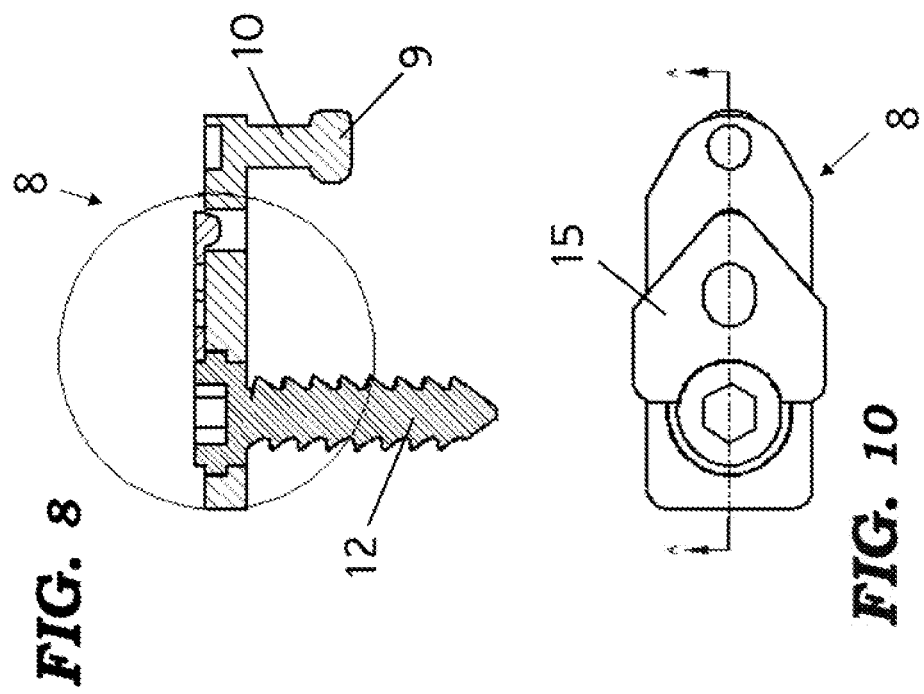

DYNAMIC INTERBODY CAGE ANCHOR SYSTEM

CROSS-REFERENCE TO RELATED APPLICATION(S)

The present application derives priority from provisional application 61/352,539, filed on Jun. 8, 2010 which is incorporated herein by reference.

BACKGROUND OF THE INVENTION

1. Field of the invention

The present invention relates generally to devices and methods for treating spinal disorders and more specifically to a system and method for securing in place an intervertebral device for aligning and maintaining the relative position of adjacent vertebrae to facilitate immobilization of the vertebra through fusion while avoiding stress shielding.

2. Description of the Background

Degeneration of the intervertebral discs and the concomitant instability and translocation of the vertebra is a common cause of back pain and may result from a variety of problems including congenital deformity, age related degeneration, osteoporosis, tumor and disc herniation as a result of trauma. Disc degeneration, for whatever reason, results in compression of the spinal nerve roots resulting in pain. Palliative care is often successful in mild cases but more extreme or degenerative cases may require a surgical approach to stabilize the joint and relieve pressure.

A number of surgical approaches have been developed with varying degrees of success depending on the cause and severity of the damage. A ruptured disc impinging the nerve root may be partially excised to relieve pressure. In such a case the adjacent vertebra may be further fixated using rods, screws and plates in an attempt to stabilize the spine and delay or prevent further degeneration. Patients undergoing such excisions and fixations however often require subsequent procedures to address recurrent pain. In many case such subsequent procedures include fusion of the adjacent vertebra. Spinal fusion, or spondylosyndesis, is a surgical technique to combine two or more vertebrae utilizing supplementary bone graft tissue in conjunction with the body's natural osteoblastic processes to eliminate relative movement as a source of pain. A variety of approaches to fusion are available including posterior fusion, postero-lateral fusion and anterior or posterior interbody fusion.

In the more traditional posterior fusion approach, growth is induced between the bony vertebral laminae to fix the position of the vertebra. In the postero-lateral fusion method bone growth is induced to join the transverse processes to prevent motion between the adjacent vertebrae. However, both posterior and postero-lateral fusion tends to cause bony overgrowth leading to nerve root compression and pain by spinal stenosis. This, coupled with other risks, limitations and disappointing fusion success rates have caused surgeons searching for alternate fusion means to develop interbody fusion techniques.

Interbody fusion techniques involve complete excision of the soft disc which is then replaced with autograft material harvested from the patient, prepared allograft from a donor source or, more recently, synthetic graft material and bone morphogenic protein. Most commonly performed in the lumbar region, the procedure can be accomplished from an anterior approach (Anterior Lumbar Interbody Fusion or ALIF) or a posterior approach (PLIF). In either case the procedure attempts to reconstruct the normal anatomic relationships between the bony and the neural structures and has many advantages. Specifically, weight bearing through a solid bony fusion mass between vertebral bodies relieves the mechanical pain of the traditional unstable degenerative disc and generally prevents long term disc collapse or further degenerative changes. The complete disc excision prevents recurrent herniation of the same degenerated disc.

Successful fusion results in a contiguous growth of bone to create a solid mass that will unite the vertebra into one unit. When fusion graft material is first placed in the intervertebral space it is soft and lacking in cohesive strength so as to be incapable of remaining in position or carrying any load without assistance. A variety of appliances have been developed that attempt to hold the vertebrae to be joined in place relative to one another under normal spinal activity and daily stress to allow the fusion process to occur over the 18-24 month period generally required. Such appliances are often referred to as interbody cages and provide a mechanically rigid scaffold in which the graft material may be placed.

Cage designs vary widely but generally fall into one of three categories. Horizontal cylinders are generally made from titanium and inserted by either the posterior or anterior approach into complimentary holes bored into the intervertebral space. They can be placed by open or minimally invasive techniques. U.S. Pat. No. 5,026,373 to Ray, et al. discloses a cage of this design that includes a perforated threaded exterior surface that can be screwed into place between the vertebra and packed with bone material. Bone growth through the perforations and into the cancellous bone of the vertebra exposed by the insertion results in the desired fusion.

A second design in the form of a vertical cylinder or ring is often referred to as a Harms cage and is also typically made from titanium. The Harms cage can be cut to length as desired so as to span larger segments of the lumbar spine. End caps are employed to prevent subsidence into the cancellous bone although this design suffers, as a result, from a requirement that its central void be pack with graft material prior to insertion. Due to its sharp edges the Harms cage is most commonly inserted by open techniques. U.S. Pat. No. 5,989,290 to Biedermann et al, et al. discloses a cage of this design.

A third design form is the open box cage. Typically constructed of carbon, titanium or bio-compatible non-metallic materials such as PEEK (Polyether ether ketone) or Delrin® (Polyoxymethylene), this design can be formed for an anatomical fit or to recreate the normal lumbar lordosis. Openings in the box walls permit graft material contained within to contact the vertebral bone. Some designs utilize a single large cage inserted by anterior approach. Alternately, a pair of smaller cages may be inserted anteriorily or posteriorily using minimally invasive techniques. U.S. Pat. No. 6,241,769 to Nicolson et al, et al. discloses a box form cage having a central void having an open top and bottom and a dovetail system for structurally attaching the device to the adjacent vertebra which are prepared by cutting cooperative channels in their surface. Other designs are secured by upper and lower flanges that are rigidly secured to the adjacent bone by screws. The applicant's own U.S. patent application number 12/660,153 filed Feb. 19, 2010 and which is incorporated herein by reference discloses a cage of this design type.

Commonly, supplementary instrumentation in the form of rods (posteriorily) or plates (anteriorily) rigidly fixed to the vertebra are also implanted to stabilize the spine and provide enhanced mechanical stability prior to fusion. These rigid appliances span the intervertebral space to maintain the intervertebral disc height and prevent excessive compression of the two vertebrae, which can lead to a weak fusion or even collapse of the graft. However, they can also lead to stress shielding, in which fusion of the vertebrae to the grafted bone is impeded or prevented entirely because the apparatus prevents adequate contact between the vertebra and the graft. Stress shielding, which occurs when plates or rods carry too large of a portion of the bone's load, refers to the reduction in bone density (osteopenia) as a result of removal of normal stress from the bone by an implant causing atrophy. Resorption of the bone graft can exacerbate this problem. It is known that some subsidence, or settling, between the vertebrae at the graft is advantageous to quickly forming a strong fusion. The subsidence increases bone to bone contact, which enhances bone fusion, as predicted by Wolff's law, by enhancing physiological processes involved in bone remodeling.

It would be therefore an improvement in this art to provide a system and method for securing an interbody fusion cage which overcomes the deficiencies of prior known systems and methods. It is an object of the present invention to provide a dynamic interbody cage anchoring system that prevents cage/graft retropulsion or lateral migration but permit axial loading thereby promoting load sharing between the vertebral column and posterior musculature and prevents stress shielding of graft material by anterior instrumentation or anteriorily fixed interbody instruments. It is a further object of the present invention to provide system and method for securing an interbody fusion cage that is sufficiently robust so as to withstand the forces imposed by normal daily activity on the part of the patient and which is adaptable to a wide variety of cage designs.

SUMMARY OF THE INVENTION

Accordingly, there is provided a system and method of securing an intervertebral fusion cage within the intervertebral space between adjacent vertebra in which one or more slots are provided in an anterior surface of the cage each extending from an oversized aperture. A retention plate having a post and enlarged head is advanced into each slot via the oversized aperture and captured therein. The post is advanced to the terminal end of the plate and secured to vertebral body at its distal end by a bone screw. A locking clip may be slideably positioned on the retention plate to prevent withdrawal of the bone screw. The slots preferably extend to the margins of the anterior surface of the cage in, for example, the pattern of an "X" or an "H". Sliding of the posts in the slots prevents the system from carrying the vertebral load (load shielding) and permits reduction in the intervertebral space to promote bone growth and fusion by graft material retained in the spacer.

The foregoing objects, features and attendant benefits of this invention will, in part, be pointed out with particularity and will become more readily appreciated as the same become better understood by reference to the following detailed description of a preferred embodiment and certain modifications thereof when taken in conjunction with the accompanying drawings.

BRIEF DESCRIPTION OF THE DRAWINGS

In the drawings:

FIG. 2a is a front/anterior perspective of an interbody cage and anchor system according to the present invention.

FIG. 2b is a section view of an interbody cage and anchor system according to the present invention.

FIG. 3 is a perspective view of a cage retaining plate according to the present invention.

FIG. 4 is a perspective view of a locking clip according to the present invention.

FIG. 5 is a perspective view of a retaining plate according to the present invention with a locking clip in place.

FIG. 6 is a perspective view of a retaining plate according to the present invention with a bone screw and retaining clip in place with the retaining clip in the open position.

FIG. 7 is a perspective view of a retaining plate according to the present invention with a bone screw and retaining clip in place with the retaining clip in the locked position.

FIG. 8 is a section view through a retaining plate and locking clip with a bone screw in place.

FIG. 9 is a detail view of FIG. 8.

FIG. 10 is a top view of an assembled retaining plate and locking clip.

FIG. 11 is perspective view of an assembled retaining plate and locking clip.

DETAILED DESCRIPTION OF THE PREFERRED EMBODIMENTS

Figure 1:
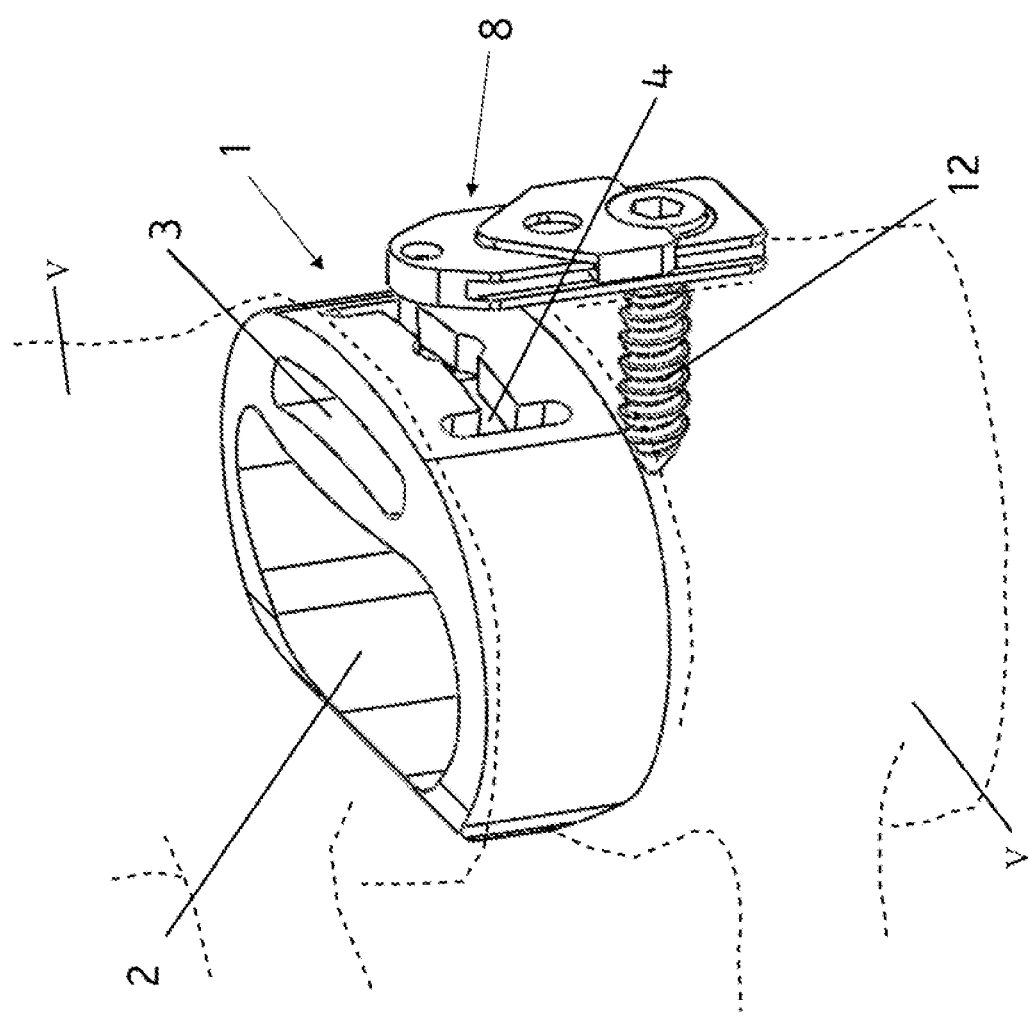
FIG. 1 is a perspective view of an interbody cage and anchor system according to the present invention.

With reference to FIG. 1, an interbody fusion cage 1 having a generally annular box form surrounding a central void 2 is provided. The void 2 extends from the upper surface of the cage to the lower surface and is provided to be packed with natural or synthetic bone graft material in order to promote bone growth and fusion of the superior and inferior vertebra V between which it will be implanted. The fusion cage 1 is preferably constructed of PEEK (Polyether ether ketone) but may be constructed of any suitable, bio-compatible material such as titanium or Polyoxymethylene. It should be noted that while the box form intervertebral cage has been used as a representative interbody spacer, a variety of interbody spacer types including horizontal and vertical cylindrical cages may also utilize the present invention.

The representative box form cage 1 is provided with a vertical surface that will be oriented to the anterior face of the spine when implanted between the adjacent vertebra V. This anterior surface need not be planar as depicted although a substantially planar surface is a preferred embodiment. Alternate embodiments utilizing flat, curved or articulated surfaces will become apparent to those skilled in the art through this disclosure. Note that the term "vertical" as used herein is meant to indicate a direction substantially parallel to the human spine in a standing position and is not intended to be limiting. A slot or series of slots 4 are provided in the anterior surface of the cage 1 in which to slideably capture a retaining plate to secure the cage within the intervertebral space. The slots 4 may be provided in the form of a single, continuous slot comprised of interconnected slot segments as depicted or may divided into a plurality of individual slots. In a depicted, preferred embodiment, the slot 4 segments are arranged and interconnected in the form of an "H" in which a vertical segment at each lateral edge of the cage is connected at its center by a horizontal segment. It should be understood that the terms "slot" and "slots" as used herein may refer to multiple, independent slots or to multiple slot segments interconnected into a single, continuous slot.

With additional reference to FIG. 2b, the narrow slot openings in the anterior surface of the cage 1 open into a second void 3 behind the slot openings in order to slideably receive and retain the enlarged head 9 of a post 10 on the bottom surface or underside of a retaining plate 8, as will further described below. The void 3 is sized to receive and permit the heads 9 to move freely within the void 3 within the limits of the slot 4. The void 3, in the depicted embodiment is a single, unitary space open to the top and bottom surfaces of the cage 1 but this need not be so and the void may be partitioned and/or closed off from the top and/or bottom of the cage. In a further, alternate embodiment the void 3 may be limited to a channel behind each slot or slot segment, the channel sized to slidingly receive each head 9. The cross section of such a channel may be circular, semicircular, or any other form having a width greater than the width of the slot and is sized and shaped to allow free movement of the head 9. In alternate embodiment the slot 4 is arranged in the form of an "X" rather than an "H" and a variety of other alternate slot arrangement will become apparent to those skilled in the art. It is preferable that the pattern of slots provide at least four terminal ends (as the "X" and "H" forms both do) and it is more preferable that one such terminal end be at or near each of the upper and lower lateral extremities of the anterior surface of the cage 1 (i.e. at the corners). Such an arrangement provides the greatest resistance to motion of the cage 1 while still permitting reduction in the interbody space.

As depicted in the embodiment of FIGS. 1 and 2a, 2b, a single, central opening 6 in the anterior surface of the cage 1 is provided for receiving the enlarged heads 9 of the plate 8. The opening 6 is preferably circular with a diameter greater than the diameter of the heads 9 so as to permit insertion of the heads although neither the heads nor the opening need be truly circular and it is sufficient that the heads 9 be able to pass through the opening 6 and into the void 3. As such the term "diameter" as used herein refers more generally to a maximum width or dimension and the maximum dimension of the opening 6 is greater than the maximum dimension of the heads 9. The opening 6 is further connected laterally to one or more of slots 4 such that heads 9 may be inserted into the opening and then slid laterally within the void 3 such that the post 10 extend through the narrow slots 4 and the assembly is slideably captured in the slot through which the post 10 may pass but the heads 9 may not. The head 9 will slide freely in the void 3 but cannot be removed without being returned to the opening 6 to be withdrawn. Where multiple, discontinuous slots 4 are provided at least one opening 6 is necessarily provided in connection with each slot in order to permit insertion and capture of a retaining plate 8.

Although only one is depicted in FIGS. 1 and 2a, 2b, a plurality of retaining plates 8 are preferably provided to secure the cage 1 to the adjacent vertebra V via the slots 4. It is preferable that a retaining plate 8 be situated at each terminal end of the slot pattern such that, as in the depicted embodiment, one is positioned at each of the corners of the "H" delineated on the anterior face of the cage 1. It will be recognized that a smaller number of retaining plates 8 including a single plate will resist motion of the cage 1 although at least one upper and one lower retaining plate is desirable and four such plates as described is preferable. The retaining plates 8 are preferably constructed of titanium but cobalt-chrome, medical grade stainless steel or other bio-compatible materials known in the art may be satisfactorily used.

With additional reference to FIGS. 3-9, the retaining plate 8 is a linear member, preferably (but not necessarily) flattened in profile and having a hole 11 at one end through which a bone screw 12 may be driven to secure the plate 8 to the vertebral body V. The length of the plate 8 will be determined by the physiology of the individual patient into which the cage 1 is being implanted and will be selected by a surgeon from a variety of available lengths at the time of implant. It is anticipated that plates 8 of differing lengths may be selected for one or more of each of the slots 4 of a particular cage 1 during implantation. The proximal end the of the plate 8 (opposite the hole 11) is provided with a post 10 terminating at a head 9 as described. The diameter of the post is less than the width of the slots 4. The length of the post will also be selected by the surgeon from a variety of lengths available at the time of implant to accommodate patient physiology and cage position within the spinal column.

The bone screw hole 11 in the plate 8 may preferably be formed to provide a countersink in which to receive the head of the bone screw 12, the term "counterbore" being used here inersink. The hea collectively to include a counterbore and a count d of the bone screw 12 is preferably seated within the counterbore such that at least a portion of its upper surface is flush with an upper surface of the plate 8, as depicted in FIG. 9. The head of the screw 12 of the embodiment depicted in FIG. 9 is provide with a protruding annular ring that is received within a concentric recess around the hole 11 (i.e. the counterbore) while a central portion of the head extends upward and proud of the surface of the plate 8. A locking clip is provided as part of the retaining plate 8 to engage the upper surface of the screw head and prevent it from backing out after insertion. The locking clip is preferably provided in form of a slide 15 engaged to the plate 8 that is able to override a portion of the screw head and preferably overrides the flush portion of the screw to thereby prevent it from backing out of the bone by counter rotation or otherwise.

In the preferred embodiment, the slide 15 is engaged to the plate 8 by a pair of cooperative runners 17 integrally formed on the underside of the clip 15 and received in a longitudinal channel 16 provided along each of the edges of the plate 8. The runners 17 wrap around the edges of the plate 8 and are slideably received within the channels 16 to secure the clip 15 to the plate 8. In this way the clip 15 is permitted to slide from a first, open position (FIG. 6) in which the clip 16 is at the proximal end of the plate (opposite the hole 11), to a second, locked position (FIGS. 7-10) in which the slide 15 is advanced over the flush portion of the surface of the screw head. In the first, open position the screw 12 is permitted to pass through the hole 11 and into the bone whereas in the second, locked position the screw 12 is locked in place and cannot be withdrawn.

The slide 15 may engage the portion of the screw that is proud of the surface of the plate 8 as a positive stop for he slide. More preferably, the range of movement of the slide 15 may also be limited by a protrusion 18 on the underside of the slide 15 that is engaged in one or more recesses in the upper surface of the plate 8 to serve as a detent. The protrusion 18 cooperatively engages the recesses 19, 20 on the upper surface or top side of the plate 8 as depicted for example, in FIGS. 3-7, and is received within the first recess 20 when the slide 15 is in the open position to prevent undesired movement of the slide during implantation. Upon insertion of the bone screw 12 though the hole 11 the locking clip slide 15 is slid toward the distal end of the retaining plate 8 to override and secure the screw head and the protrusion is consequently relocated to the second recess 19. Relocation of the protrusion 18 is facilitated by resilient deformation of the slide 15 which bends to permit the protrusion to be withdrawn from one recess 19, 20 and springs back into place to insert and maintain the protrusion in the other recess thereby retaining the slide 15 in the desired position.

In use, the surgeon first implants the interbody cage 1 as desired through known surgical techniques with the caveat that the anterior face of the cage be anteriorily aligned and accessible. Once the cage is satisfactorily positioned the surgeon inserts the head 9 of a first retaining plate 8 into the void 3 via the opening 6 and slides the post along the first slot 4 to its terminal end. The surgeon then secures the opposite end of the retaining plate 8 to the bone by driving a bone screw 12 through hole 11. When the bone screw 12 is fully seated and tightened into the bone to the surgeons satisfaction the screw is secured and prevented from backing out of position by moving the slide 15 from the unlocked position to the locked position overriding at least a portion of the head of the screw 12 within the countersunk screw hole 11. The surgeon repeats this procedure until a retaining plate 8 is positioned at the terminal end of each slot and secured to the adjacent bone. It should be noted that the retaining plates 8 may be vertically oriented/aligned with the spine (as in FIG. 2*a*) or may be angled laterally from the vertical to a degree to promote stability and to accommodate patient physiology. The retaining plates 8 prevent rotation and retropulsion of the cage 1 and significantly resists lateral translation of the spacer, particularly when angled from the vertical. However, because the posts 10 can slide in the slots 4, the system does not carry the vertical load placed on the vertebral bodies of the spine. Rather, as the cage subsides into the bone, the posts 10 slide in the slots 4 and the intervertebral space is automatically reduced to maintain the normal loading on the graft material packed in the void 2.

It is observed that the alignment of the slots 4 may be further chosen to manage load sharing between the vertebral body and the device. For example, where the described "H" arrangement is utilized (as in FIG. 1) substantially no resistance to intervertebral reduction is provided because the terminal segments of the slot 4 are entirely vertical and the vertebral body and offers no resistance to vertical movement of the posts. Consequently, substantially the entire load is transferred through the interbody space. However, where the "X" slot arrangement is used the terminal segments of the slot have a horizontal vector component (i.e. they are sloped from the vertical), such that the post 10 will engage the surface of the slot and transfer some load from the vertebral bodies to the instrument. In such an arrangement, limited rotation of the retaining plate 8 around the screw 12 may be permitted to facilitate and manage load sharing. In a further embodiment the slots 4 may be curved to provide a varying load sharing provide. In such an embodiment, zero initial load capacity may be provided by substantially vertical terminal slot ends. Moving away from the terminal slot ends the slot gradually curves from the vertical to the horizontal such that the resistance and load carrying capacity of the appliance gradually increasing with additional subsidence until a maximum is reached at which most of the vertical load bypasses the interbody space.

It should be understood that the disclosure of this application may be used with a variety of interbody spacer forms and designs and with a variety of bone screw designs and sizes. It should also be understood that the disclosure may be constructed of a variety of suitable surgical grade materials including stainless steel and titanium as well as composite materials having suitable strength and corrosion resistance properties should such materials be approved for surgical implantation. This application is therefore intended to cover any variations, uses, or adaptations of the invention using its general principles. Further, this application is intended to cover such departures from the present disclosure as come within known or customary practice in the art to which this invention pertains.

We claim:

1. A system for securing a fusion cage with an anteriorly oriented surface between adjacent vertebrae comprising:
    in said anteriorly oriented surface, an opening and at least two slots in operative engagement with said opening and extending therefrom, each of said at least two slots having a terminal segment aligned to have at least a vertical vector component; and
    in a first of said at least two slots, a first retaining member having a first end slideably retained in said terminal segment and a second end fixedly secured only to a superior adjacent vertebra by a bone screw
    in a second of said at least two slots, a second retaining member independent from said first retaining member and having a first end slideably retained in said terminal segment and a second end fixedly secured only to an inferior adjacent vertebra by a bone screw
    whereby engagement of said first ends of said retaining members in said terminal segments distributes a selective portion of a load on one of said adjacent vertebrae directly to another of said adjacent vertebrae.

2. The system for securing a fusion cage between adjacent vertebrae of claim 1, wherein each of said first and second retaining member further comprises
    a post at said first end, said post having a diameter less than a width of said at least two slots and terminating in a head, said head having a diameter greater than the width of said at least two slots; and
    a hole through said second end for receiving a bone screw;
    whereby said retaining members are slideably engaged to said cage by insertion of said heads into said opening and capture of said posts in said slots.

3. The system for securing a fusion cage between adjacent vertebrae of claim 2, further comprising a locking clip engaged to each retaining member, each said locking clip comprising a
    a slide engaged to a top surface of said retaining member and moveable between a first position in which movement of said bone screw though said hole is permitted, and a second position in which said slide overrides said bone screw such that said bone screw cannot be withdrawn.

4. The system for securing a fusion cage between adjacent vertebrae of claim 3, wherein each said retaining member further comprises at least one longitudinal channel and wherein said slide further comprises at least one runner engaged in said at least one longitudinal channel whereby said slide is maintained in engagement with said top surface of said retaining clip but moveable between said first position and said second position.

5. The system for securing a fusion cage between adjacent vertebrae of claim 4 wherein said at least one longitudinal channel comprises two longitudinal channels, one of said two opposing channels provided on each of two opposing sides of each of said retaining members, and wherein said at least one runner is two runners, one of which is engaged in each of said two channels.

6. The system for securing a fusion cage between adjacent vertebrae of claim 5 wherein each said retaining member is planar and wherein said two longitudinal channels are positioned on opposing edges of said members.

7. The system for securing a fusion cage between adjacent vertebrae of claim 6 wherein each said planar retaining member further comprises at least one recess on said top surface, and wherein said slide further comprises a protrusion for engagement in said recess whereby a bias is imposed on said slide to inhibit said sliding motion.

8. The system for securing a fusion cage between adjacent vertebrae of claim 7 wherein said at least one recess comprises two recess for engagement by said protrusion wherein a first recess is engaged by said protrusion when said slide is in said first position and a second recess is engaged by said protrusion when said slide is in said second position.

9. The system for securing a fusion cage between adjacent vertebrae of claim 2 wherein each said hole further comprises a counterbore and wherein said bone screw is cooperatively formed with a head to be received in said counterbore such that at least a portion of said head is flush with said top surface of said retaining member.

10. The system for securing a fusion cage between adjacent vertebrae of claim 1 wherein said at least two slots comprises four slots in the form of an "H".

11. The system for securing a fusion cage between adjacent vertebrae of claim 1 wherein said at least two slots comprises four slots in the form of an "X".

12. The system for securing a fusion cage between adjacent vertebrae of claim 1 wherein said terminal segment of each of said at least two slots is substantially vertical and wherein each said slot is curved therefrom toward a horizontal alignment.

* * * * *